(12) United States Patent
Baek et al.

(10) Patent No.: US 10,750,982 B2
(45) Date of Patent: Aug. 25, 2020

(54) OXYGEN SATURATION MEASURING APPARATUS AND OXYGEN SATURATION MEASURING METHOD THEREOF

(71) Applicant: SAMSUNG ELECTRONICS CO., LTD., Suwon-si, Gyeonggi-do (KR)

(72) Inventors: Hyun-jae Baek, Seoul (KR); Jae-wook Shin, Suwon-si (KR); Jae-geol Cho, Yongin-si (KR); Gun-woo Jin, Suwon-si (KR); Byung-hun Choi, Suwon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 288 days.

(21) Appl. No.: 15/366,461

(22) Filed: Dec. 1, 2016

(65) Prior Publication Data

US 2017/0181680 A1     Jun. 29, 2017

(30) Foreign Application Priority Data

Dec. 24, 2015  (KR) .................. 10-2015-0186453

(51) Int. Cl.
*A61B 5/1455* (2006.01)
*A61B 5/00* (2006.01)
*A61B 5/024* (2006.01)

(52) U.S. Cl.
CPC ...... *A61B 5/14551* (2013.01); *A61B 5/02416* (2013.01); *A61B 5/02438* (2013.01);
(Continued)

(58) Field of Classification Search
CPC . A61B 5/14551; A61B 5/725; A61B 5/02438; A61B 5/02416; A61B 5/742;
(Continued)

(56) References Cited

U.S. PATENT DOCUMENTS

| 5,025,791 A | * | 6/1991 | Niwa | ................. | A61B 5/14552 |
|---|---|---|---|---|---|
| | | | | | 600/324 |
| 7,215,984 B2 | | 5/2007 | Diab et al. | | |

(Continued)

FOREIGN PATENT DOCUMENTS

| JP | 2003-135434 | 5/2003 |
|---|---|---|
| JP | 2004-202190 | 7/2004 |

(Continued)

OTHER PUBLICATIONS

Search Report and Written Opinion dated Mar. 14, 2017 in counterpart International Patent Application No. PCT/KR2016/014094.

*Primary Examiner* — Eric F Winakur
*Assistant Examiner* — Abid A Mustansir
(74) *Attorney, Agent, or Firm* — Nixon & Vanderhye P.C.

(57) ABSTRACT

An oxygen saturation measuring apparatus is provided. The oxygen saturation measuring apparatus includes a sensor configured to detect motion of the oxygen saturation measuring apparatus, a light emitter comprising light emitting circuitry configured to emit light to a target subject, a light receiver comprising light receiving circuitry configured to receive one or more of light reflected by the target subject or light transmitted through the target subject to generate a signal, and a processor configured to filter a frequency component corresponding to the detected motion in the signal, to detect a pulse frequency from the filtered signal, and to determine oxygen saturation of the target subject using the filtered signal and the detected pulse frequency.

20 Claims, 15 Drawing Sheets

(52) U.S. Cl.
CPC .............. *A61B 5/721* (2013.01); *A61B 5/725* (2013.01); *A61B 5/7225* (2013.01); *A61B 5/742* (2013.01); *A61B 5/681* (2013.01); *A61B 5/6826* (2013.01); *A61B 5/6898* (2013.01)

(58) Field of Classification Search
CPC ..... A61B 5/721; A61B 5/7225; A61B 5/6826; A61B 5/681; A61B 5/6898
See application file for complete search history.

(56) References Cited

U.S. PATENT DOCUMENTS

| | | | | |
|---|---|---|---|---|
| 2003/0055325 | A1* | 3/2003 | Weber | A61B 5/024 600/323 |
| 2003/0065269 | A1* | 4/2003 | Vetter | A61B 5/02416 600/503 |
| 2003/0229276 | A1* | 12/2003 | Sarussi | A61B 5/02433 600/322 |
| 2004/0225207 | A1 | 11/2004 | Bae et al. | |
| 2009/0036762 | A1 | 2/2009 | Tateda et al. | |
| 2010/0198027 | A1* | 8/2010 | Dixon | A61B 5/14551 600/323 |
| 2012/0253156 | A1* | 10/2012 | Muhlsteff | A61B 5/02416 600/324 |
| 2012/0271121 | A1 | 10/2012 | Della Torre et al. | |
| 2013/0303922 | A1* | 11/2013 | Buchheim | A61B 5/02416 600/479 |
| 2014/0200423 | A1 | 7/2014 | Eisen et al. | |
| 2014/0243627 | A1* | 8/2014 | Diab | A61B 5/14551 600/323 |
| 2015/0065889 | A1* | 3/2015 | Gandelman | A61B 5/02427 600/479 |
| 2015/0196257 | A1* | 7/2015 | Yousefi | A61B 5/024 600/324 |

FOREIGN PATENT DOCUMENTS

| | | |
|---|---|---|
| JP | 2009-034427 | 2/2009 |
| KR | 10-0870773 | 11/2008 |
| KR | 10-2011-0000797 | 1/2011 |
| KR | 2012-0126473 | 11/2012 |

* cited by examiner

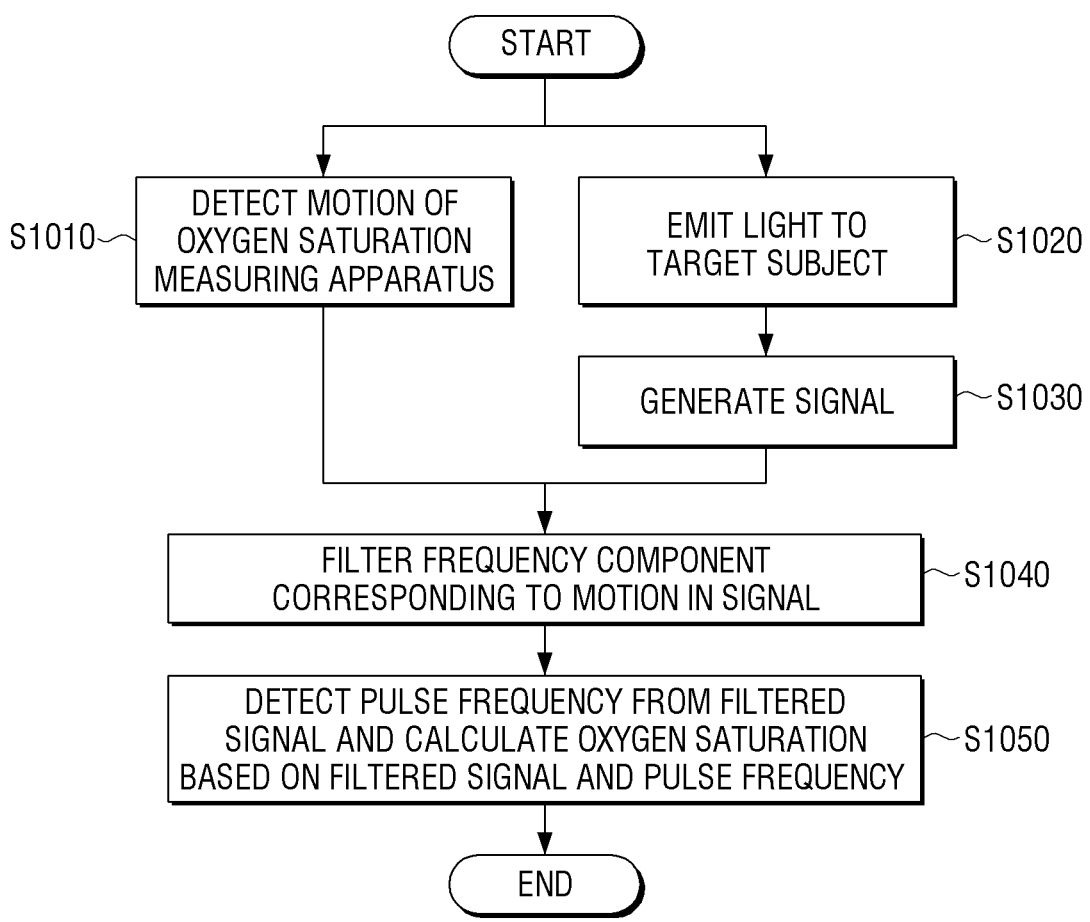

OXYGEN SATURATION MEASURING APPARATUS AND OXYGEN SATURATION MEASURING METHOD THEREOF

CROSS-REFERENCE TO RELATED APPLICATION

This application is based on and claims priority under 35 U.S.C. § 119 to Korean Patent Application No. 10-2015-0186453, filed on Dec. 24, 2015 in the Korean Intellectual Property Office, the disclosure of which is incorporated by reference herein in its entirety.

BACKGROUND

Field

The present disclosure relates generally to an oxygen saturation measuring apparatus and an oxygen saturation measuring method thereof, and for example, to an oxygen saturation measuring apparatus and an oxygen saturation measuring method thereof, for accurately measuring oxygen saturation in a mobile environment.

Description of Related Art

A conventional technology for measuring oxygen saturation includes 1) an invasive method of collecting arterial blood and directly analyzing oxygen saturation and 2) a non-invasive method of measuring light absorption when hemoglobin in blood is combined with oxygen and light absorption when hemoglobin is not combined with oxygen and measuring oxygen saturation using a ratio therebetween.

The method of collecting arterial blood and measuring oxygen saturation in the blood is capable of measuring a most accurate oxygen saturation value but has a problem in that a patient feels pain during blood collection and current oxygen saturation of blood of the patient is not capable of being acquired in real time because a predetermined time is taken to collect blood and to analyze an oxygen saturation value.

On the other hand, the non-invasive method of measuring oxygen saturation in blood does not cause pain to a patient by virtue of non-invasive measurement and is also capable of acquiring oxygen saturation in blood in real time and, thus, has been broadly used in environments outside a hospital as well as in clinical environments.

In detail, the non-invasive method of measuring oxygen saturation is a method of emitting red light and near infrared light on a sample, converting light that is not absorbed into the sample into an electrical signal, and measuring oxygen saturation. According to such a conventional technology, a peak and a valley need to be detected in a pulse according to each heartbeat in the time domain and, thus, the result is greatly affected by a signal to noise ratio (SNR) of a signal.

However, in environments outside a hospital, since an external light source such as sunlight or lighting is major influence and motion artifact due to motion such as arm motion or walking motion is a major influence, it is difficult to accurately detect a peak and a valley and, accordingly, there is a problem in that accurately of oxygen saturation is degraded.

In particular, when a reflection type sensor is used on a body surface like a wrist watch, it is difficult to ensure a robust contact state between a sensor and a skin surface as compared with a transmission type sensor used in the form of a clip at a finger and an SNR of a pulse wave signal measured by applying relatively large motion is remarkably lowered and, thus, detected peak and valley values are not accurate.

FIG. 1 is a diagram illustrating an example of a waveform of a pulse wave due to noise caused by an external light source or noise caused by contact inferiority between a finger and a sensor in a transmission type sensor (A left portion shows a signal of light in a near infrared wavelength and a right portion shows a signal of light in a red wavelength.). In this case, it is not possible to accurately detect peak and valley values and, thus, a serious error is caused in a calculated oxygen saturation value.

FIG. 2 is a diagram illustrating an example of a waveform of a pulse wave signal measured from a wrist-type device. When the pulse wave signal is measured in a state without motion, a pulse wave is clearly measured according to pulsation as illustrated in a left portion of FIG. 2 but, when there is wrist motion caused by walking, running, or the like, a motion artifact due to motion more largely overlaps than pulsation components and, thus, it is not possible to detect peak and valley values, as illustrated in a right portion of FIG. 2.

Accordingly, there is a need for a method of measuring accurate oxygen saturation even in an environment in which there is noise due to an external light source and noise due to motion.

SUMMARY

Example embodiments of the present disclosure address the above disadvantages and other disadvantages not described above.

The present disclosure provides an oxygen saturation measuring apparatus and an oxygen saturation measuring method thereof, for more accurately measuring oxygen saturation in a mobile environment.

According to an example aspect of the present disclosure, an oxygen saturation measuring apparatus includes a sensor configured to detect motion of the oxygen saturation measuring apparatus, a light emitter comprising light emitting circuitry configured to emit light to a target subject, a light receiver comprising light receiving circuitry configured to receive light reflected by the target subject or transmitted through the target subject to generate a signal, and a processor configured to filter a frequency component corresponding to the detected motion in the signal, to detect a pulse frequency from the filtered signal, and to determine oxygen saturation of the target subject using the filtered signal and the detected pulse frequency.

The processor may separate a signal component corresponding to the detected pulse frequency from the filtered signal and determine oxygen saturation of the target subject based on the separated signal component.

The processor may separate the signal component from the filtered signal through a comb filter corresponding to the detected pulse frequency.

The light emitter may include a first light emitting device for emitting light of a first wavelength and a second light emitting device for emitting light of a second wavelength different from the first wavelength.

The processor may filter a frequency component corresponding to the detected motion in a signal corresponding to light of the first wavelength, filter a frequency component corresponding to the detected motion in a second signal corresponding to light of the second wavelength, detect a first pulse frequency from the filtered first signal, separate a first signal component corresponding to the first pulse frequency from the filtered first signal, separate a second signal component corresponding to first pulse frequency from the filtered second signal, and determine oxygen saturation of the target subject based on the first signal component and the second signal component.

The processor may filter a frequency component corresponding to the detected motion in a first signal corresponding to light of the first wavelength, filter a frequency component corresponding to the detected motion in a second signal corresponding to light of the second wavelength, detect a first pulse frequency from the filtered first signal, detect a second pulse frequency from the filtered second signal, separate a first signal component corresponding to the first pulse frequency from the filtered first signal, separate a second signal component corresponding to the second pulse frequency from the filtered second signal, and determine oxygen saturation of the target subject based on the first signal component and the second signal component.

The sensor may include at least one of an acceleration sensor, a gyro sensor, and a geomagnetic sensor.

The oxygen saturation measuring apparatus may further include a display configured to display the determined oxygen saturation.

The processor may control the display to display the filtered signal.

The processor may control the display to display information on the detected pulse frequency.

The oxygen saturation measuring apparatus may be a smartphone or a wearable device.

According to an example embodiment of the present disclosure, an oxygen saturation measuring method of an oxygen saturation measuring apparatus includes detecting motion of the oxygen saturation measuring apparatus, emitting light to a target subject, receiving light reflected by the target subject or transmitted through the target subject to generate a signal, filtering a frequency component corresponding to the detected motion in the signal, and detecting a pulse frequency from the filtered signal and determining oxygen saturation of the target subject using the filtered signal and the detected pulse frequency.

The determining of the oxygen saturation may include separating a signal component corresponding to the detected pulse frequency from the filtered signal and determining oxygen saturation of the target subject based on the separated signal component.

The determining of the oxygen saturation may include separating the signal component from the filtered signal through a comb filter corresponding to the detected pulse frequency.

The emitting may include emitting light of a first wavelength and light of a second wavelength different from the first wavelength to the target subject.

The filtering may include filtering a frequency component corresponding to the detected motion in a first signal corresponding to light of the first wavelength and filtering a frequency component corresponding to the detected motion in a second signal corresponding to the second wavelength, and the determining of the oxygen saturation may include detecting a first pulse frequency from the filtered first signal, separating a first signal component corresponding to the first pulse frequency from the filtered first signal, separating a second signal component corresponding to the first pulse frequency from the filtered second signal, and determining oxygen saturation of the target subject based on the first signal component and the second signal component.

The filtering may include filtering a frequency component corresponding to the detected motion in a first signal corresponding to light of the first wavelength and filtering a frequency component corresponding to the detected motion in a second signal corresponding to light of the second wavelength, the determining of the oxygen saturation may include detecting a first pulse frequency from the filtered first signal, detecting a second pulse frequency from the filtered second signal, separating a first signal component corresponding to the first pulse frequency from the filtered first signal, separating a second signal component corresponding to the second pulse frequency from the filtered second signal, and determining oxygen saturation of the target subject based on the first signal component and the second signal component.

The method may further include displaying the determined oxygen saturation.

The method may further include displaying the filtered signal.

According to an example embodiment of the present disclosure, a computer readable recording medium has recorded thereon a program for executing the method including detecting motion of the oxygen saturation measuring apparatus, emitting light to a target subject, receiving light reflected by the target subject or transmitted through the target subject to generate a signal, filtering a frequency component corresponding to the detected motion in the signal, and detecting a pulse frequency from the filtered signal and determining oxygen saturation of the target subject using the filtered signal and the detected pulse frequency.

Additional and/or other aspects and advantages of the disclosure will be set forth in part in the description which follows and, in part, will be apparent from the description.

BRIEF DESCRIPTION OF THE DRAWINGS

The above and/or other aspects of the present disclosure will be more readily apparent from the following detailed description, taken in conjunction with the accompanying drawings, in which like reference numerals refer to like elements, and wherein:

FIG. 10 is a flowchart illustrating an example method of measuring oxygen saturation of an oxygen saturation measuring apparatus according to an example embodiment of the present disclosure.

DETAILED DESCRIPTION

Various example embodiments of the present disclosure will now be described in greater detail with reference to the accompanying drawings. In the following description of the present disclosure, a detailed description of known functions and configurations incorporated herein may be omitted when it may make the subject matter of the present disclosure unclear. The terms used in the disclosure are defined in consideration of functions used in the present disclosure, and can be changed based on the intent or conventionally used methods. Accordingly, definitions of the terms should be understood on the basis of the entire description of the present disclosure The terms such as "first" and "second" are used herein merely to describe a variety of constituent elements, but the constituent elements are not limited by the terms. The terms are used only for the purpose of distinguishing one constituent element from another constituent element.

The terms used in the present disclosure are used for explaining various example embodiments, not for limiting the present disclosure. Thus, the singular expressions in the present disclosure include the plural expressions unless clearly specified otherwise in context. Also, the terms such as "include" or "comprise" may be understood to denote a certain characteristic, number, step, operation, constituent element, or a combination thereof, but may not be construed to exclude the existence of or a possibility of addition of one or more other characteristics, numbers, steps, operations, constituent elements, or combinations thereof.

In example embodiments of the present disclosure, terms such as 'unit' or 'module', etc., should be understood as a unit that performs at least one function or operation and may be embodied in a hardware manner, a software manner, or a combination of the hardware manner and the software manner. In addition, a plurality of "units" may be integrated into at least one module to be embodied as at least one processor including processing circuitry, a dedicated processor, or the like, except for a "unit" required to be embodied in a specific hardware manner.

Figure 1:
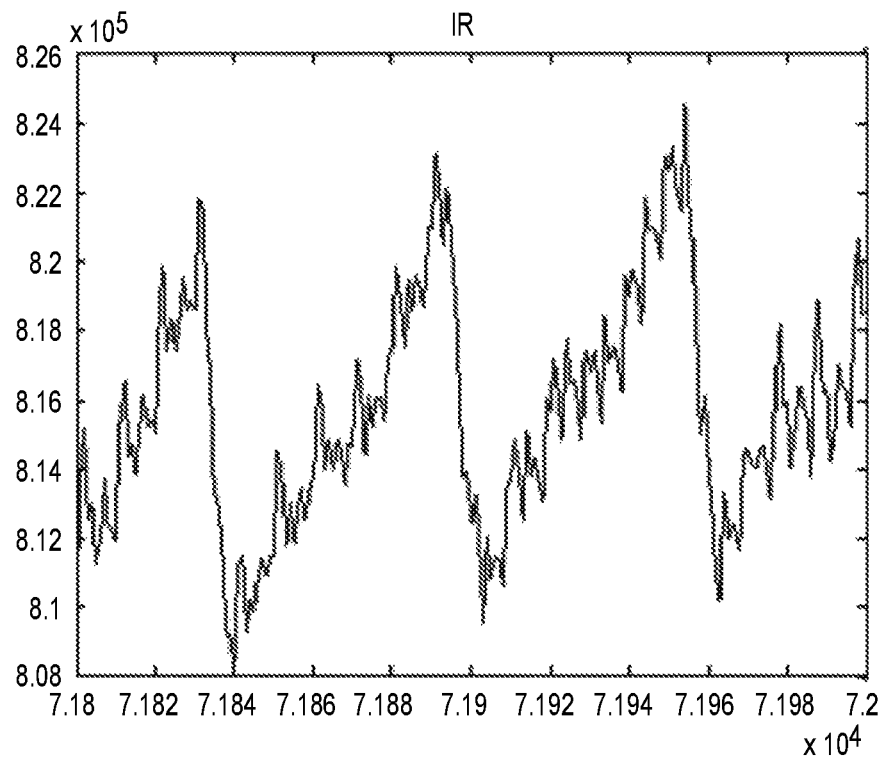
FIG. 1 is a diagram illustrating an example of a waveform of a pulse wave due to noise caused by an external light source or noise caused by contact inferiority between a finger and a sensor, measured by a conventional oxygen saturation measuring apparatus.
Figure 1:
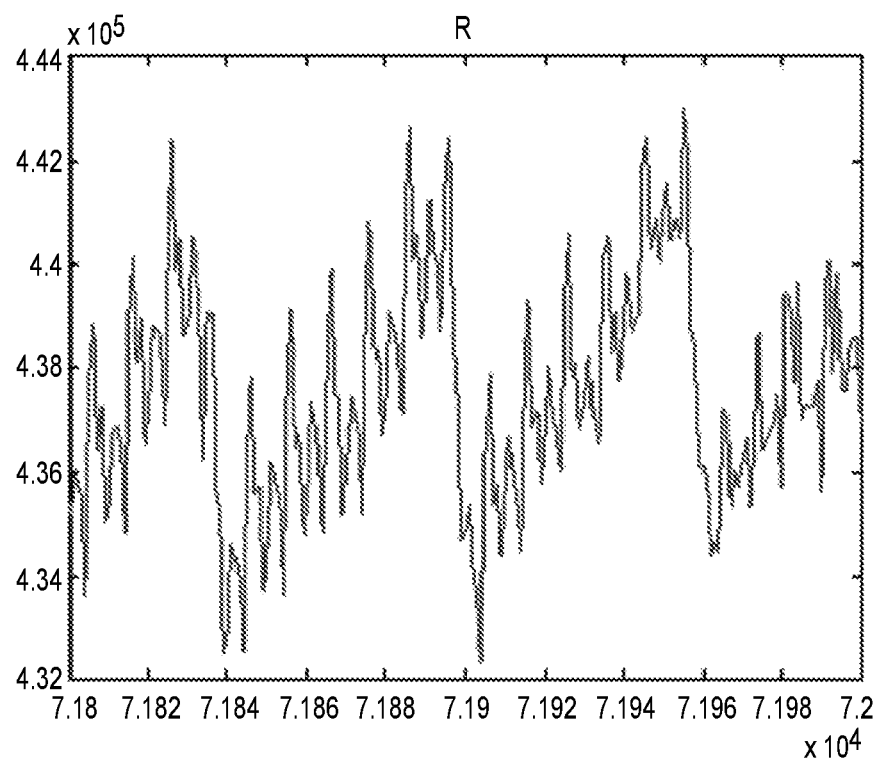
Figure 2:
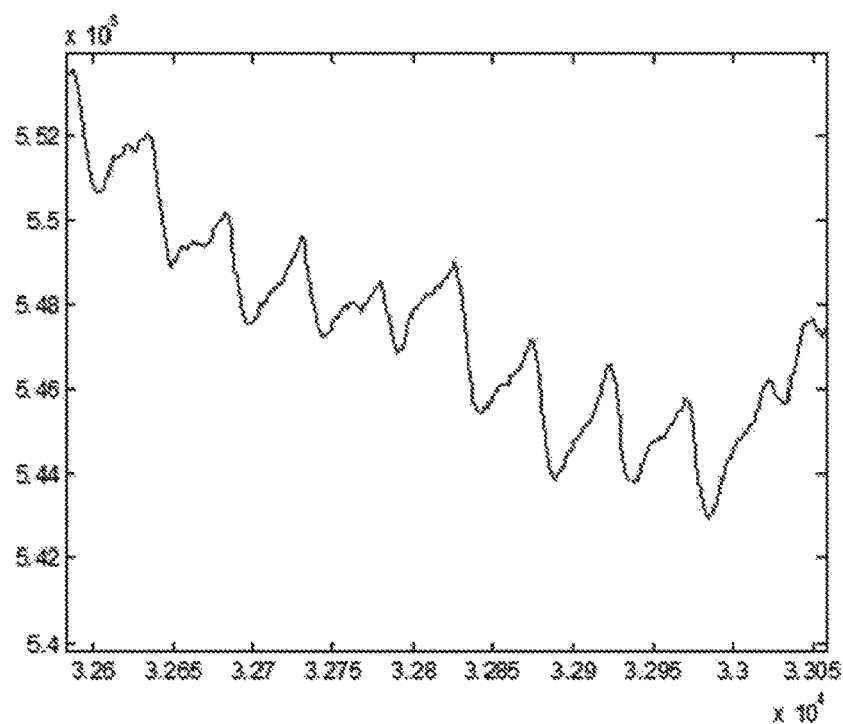
FIG. 2 is a diagram illustrating an example of a waveform of a pulse wave signal measured without motion and with motion by a conventional oxygen saturation measuring apparatus.
Figure 2:
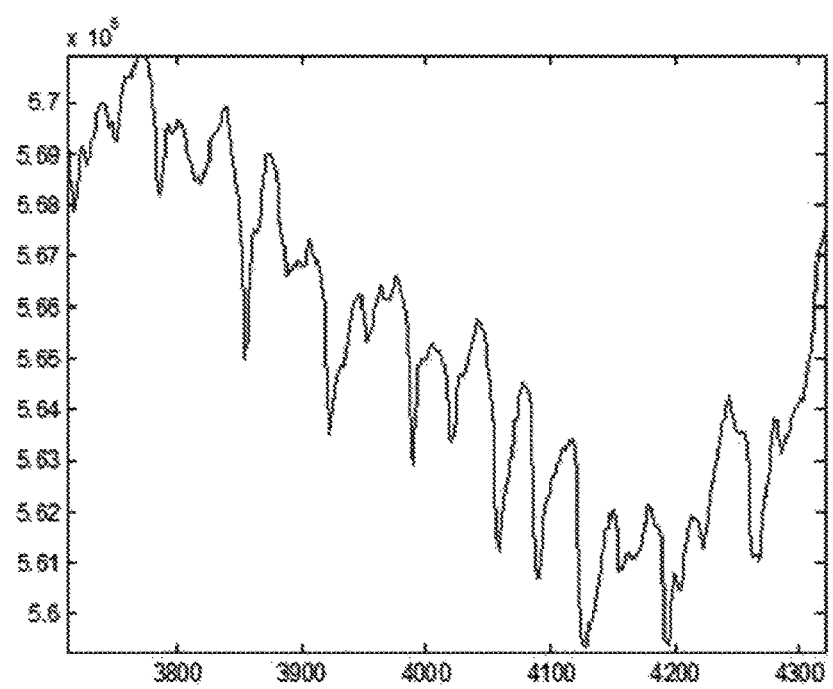
Figure 3:
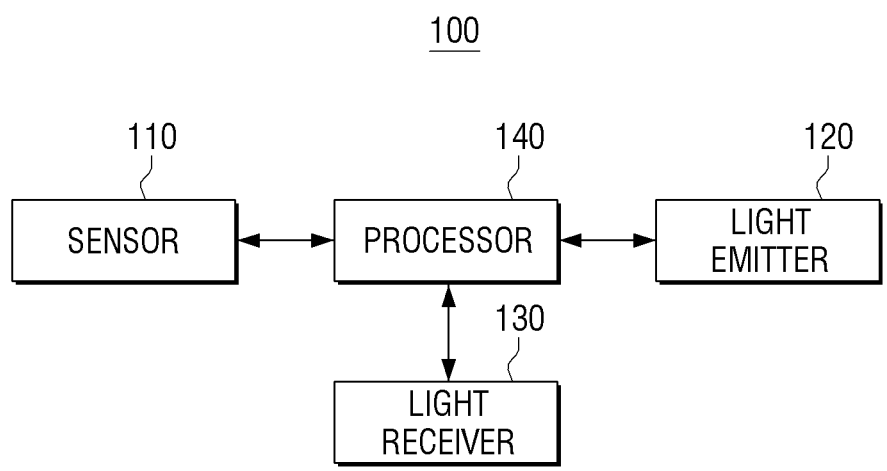
FIG. 3 is a block diagram illustrating an example oxygen saturation measuring apparatus according to an example embodiment of the present disclosure.

FIG. 3 is a block diagram illustrating an example oxygen saturation measuring apparatus 100 according to an example embodiment of the present disclosure.

Referring to FIG. 3, the oxygen saturation measuring apparatus 100 may include a sensor 110, a light emitter (e.g., including light emitting circuitry) 120, a light receiver (e.g., including light receiving circuitry) 130, and a processor (e.g., including processing circuitry) 140.

The oxygen saturation measuring apparatus 100 measures oxygen saturation (SpO$_2$) without directly colleting blood, and instead using optical properties of hemoglobin combined with oxygen in blood and hemoglobin that is not combined with oxygen.

The oxygen saturation represents a ratio of concentration of oxidized hemoglobin combined with oxygen to total hemoglobin concentration.

For example, the oxygen saturation measuring apparatus 100 measures a photo-plethysmography (PPG) signal and measures oxygen saturation (SpO$_2$) of a target subject. For example, the target subject may be a living animal including a human, and the oxygen saturation measuring apparatus 100 may be allowed to contact a specific part of the target subject, for example, a body part through which artery passes, such as a finger end so as to noninvasively measure oxygen saturation in blood.

The oxygen saturation measuring apparatus 100 may also be referred to as a pulse oximeter.

Figure 4:
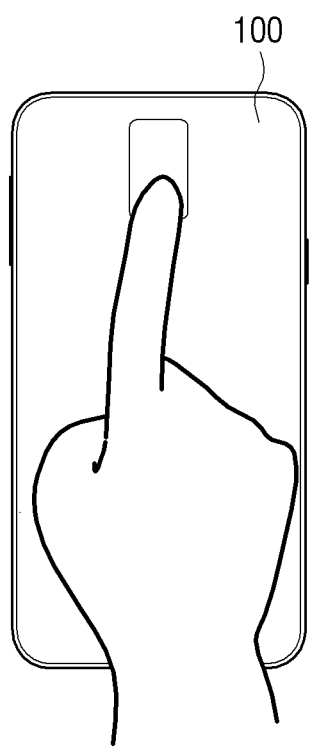
FIGS. 4 to 6 are diagrams illustrating examples of various example oxygen saturation measuring apparatuses according to various example embodiments of the present disclosure.

The oxygen saturation measuring apparatus 100 may be, for example, a smartphone. FIG. 4 is a diagram illustrating an example in which the oxygen saturation measuring apparatus 100 is a smartphone.

Figure 5:
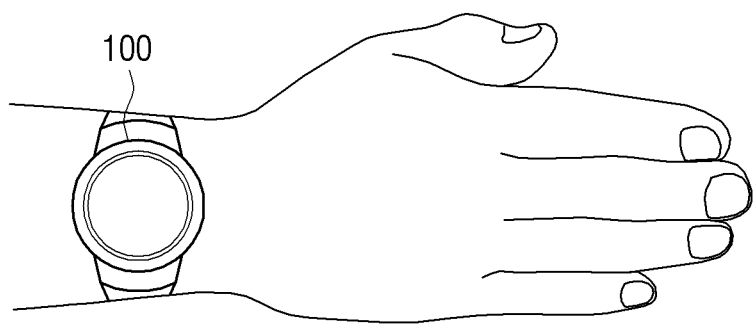

According to another example embodiment of the present disclosure, the oxygen saturation measuring apparatus 100 may be a wearable device. The wearable device may refer, for example, to a device wearable by a user. For example, the wearable device may be various types of devices wearable on a body of the human or animal, such as clothes, shoes, gloves, glasses, watches, bracelet, and accessory, or the like. FIG. 5 is a diagram illustrating an example in which the oxygen saturation measuring apparatus 100 is a wearable device such as a smart watch.

Figure 6:
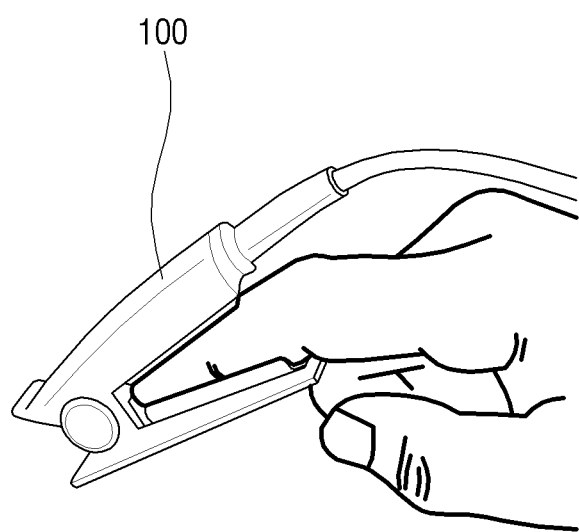

According to another example embodiment of the present disclosure, the oxygen saturation measuring apparatus 100 may be a clip-type apparatus put on a finger as illustrated in FIG. 6. The type of the oxygen saturation measuring apparatus 100 is not limited to the aforementioned examples and may have various other types.

The sensor 110 may be a component for detecting motion of the oxygen saturation measuring apparatus 100. For example, and without limitation, the sensor 110 may include at least one of a gyro sensor, a geomagnetic sensor, and an acceleration sensor.

The acceleration sensor senses an inclination degree using gravity. For example, when a gravity value corresponding to sensing in a vertical direction is 1 g, if an object is obliquely inclined, a value less than 1 g may be acquired, and if the object stands upside down, a value of −1 g may be acquired. The acceleration sensor may output a pitch angle and a roll angle based on this principle. The acceleration sensor may, for example, use a 2-axis or 3-axis flux-gate.

The geomagnetic sensor may, for example, be a device for measuring the intensity and direction of terrestrial magnetism and, for example, a geomagnetic sensor using a flux-gate may be referred to as a flux-gate type geomagnetic sensor. The geomagnetic sensor may also be embodied as a 2-axis or 3-axis flux-gate sensor like the acceleration sensor.

The gyro sensor may, for example, detect angular velocity and sense an inclination degree around a rotational axis according to Coriolis force. As the gyro sensor, both a mechanical sensor and an electronic sensor may be used.

The sensor 110 may generate a signal corresponding to detected motion. The generated signal may be used to filter a motion artifact of a signal as will be described in greater detail below.

The light emitter 120 may be a component for emitting light to a target subject. The light emitter 120 may be a general light emitting diode or laser diode. The light emitter 120 may be referred to herein as light emitting circuitry and may include, without limitation, one or more of a general light emitting diode, laser diode, or the like.

The light emitter 120 may include a plurality of light emitting devices for emitting light with different wavelengths. The light emitter 120 may include a plurality of light emitting devices for emitting light with two different wavelengths in the range of 600 to 1100 nm based on the properties of light absorption of hemoglobin during measurement of oxygen saturation.

For example, the light emitter 120 may include a first light emitting device for emitting light of a first wavelength and a second light emitting device for emitting light of a second wavelength different from the first wavelength. In this example, the first wavelength may be a red wavelength, e.g., about 660 nm and the second wavelength may be a wavelength of a near infrared band, e.g., about 940 nm. It may be possible to use two or more wavelengths.

The light receiver 130 may receive light and perform photoelectric conversion on the received light to generate a current signal. The light receiver 130 may be a general photo diode. The light receiver 130 may be referred to herein as light receiving circuitry and may include, without limitation, a general photo diode.

The light receiver 130 may receive light that is emitted from the light emitter 120 and reflected from a target object. In addition, the light receiver 130 may receive light that is emitted from the light emitter 120 and transmitted through the target object.

In order to receive the light transmitted through the target object, the oxygen saturation measuring apparatus 100 may be configured in such a way that the light receiver 130 is disposed to face the light emitter 120. For example, like the oxygen saturation measuring apparatus 100 of a clip type illustrated in FIG. 6, the light receiver 130 may be disposed at one side of the clip and the light emitter 120 may be disposed at another side. In the clip-type apparatus illustrated in FIG. 6, the sensor 110, the light emitter 120, and the light receiver 130 may be disposed and the processor 140 for processing a signal may be connected to the clip-type apparatus illustrated in FIG. 6 by wire or wirelessly.

In order to receive light reflected from the target object, the oxygen saturation measuring apparatus 100 may be configured in such a way that the light receiver 130 and the light emitter 120 may be disposed on the same surface. For example, the oxygen saturation measuring apparatus 100 illustrated in FIG. 4 may be configured in such a way that the light receiver 130 and the light emitter 120 are disposed on the same surface below a finger. The oxygen saturation measuring apparatus 100 illustrated in FIG. 5 may be configured in such a way that the light receiver 130 and the light emitter 120 are disposed on the same surface of a rear surface of a watch.

When a method of receiving light reflected from a target object is used, the oxygen saturation measuring apparatus 100 may be referred to as a reflection pulse oximeter and, when a method of receiving light transmitted through the target object is used, the oxygen saturation measuring apparatus 100 may be referred to as a transmission pulse oximeter.

Figure 7:
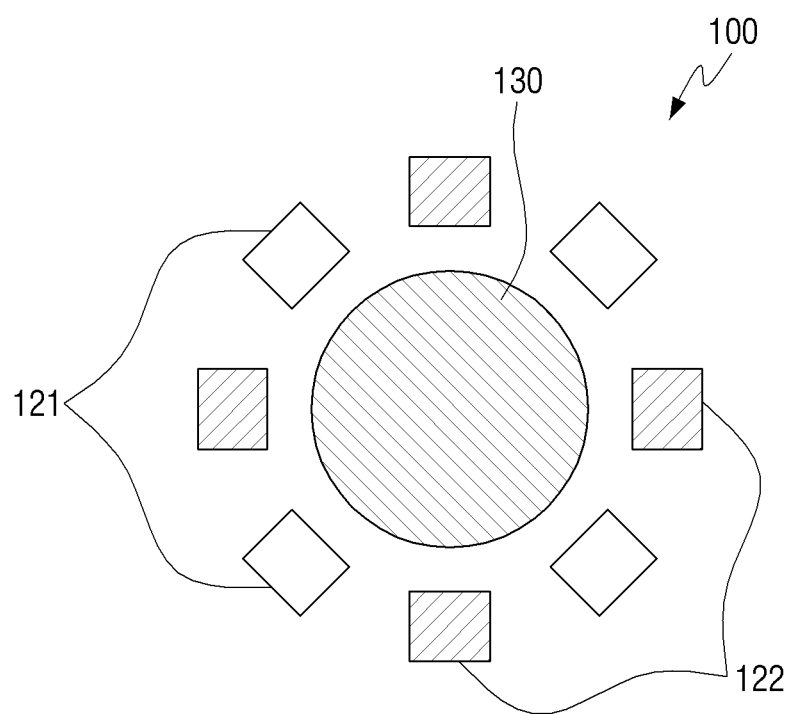
FIG. 7 is a diagram illustrating an example arrangement of a light emitter and a light receiver according to an example embodiment of the present disclosure.

The aforementioned light emitter 120 and light receiver 130 may be spaced apart from each other on the oxygen saturation measuring apparatus 100. FIG. 7 is a diagram illustrating an example arrangement of the light emitter 120 and the light receiver 130 according to an example embodiment of the present disclosure.

FIG. 7 is a diagram illustrating an example in which the light emitter 120 and the light receiver 130 are disposed on the same surface. That is, the oxygen saturation measuring apparatus 100 may correspond to the aforementioned reflection pulse oximeter.

Referring to FIG. 7, the light emitter 120 and the light receiver 130 may be disposed on one surface of the oxygen saturation measuring apparatus 100 and the light emitter 120 may include first light emitting devices 121 for emitting light in a first wavelength and second light emitting devices 122 for emitting light in a second wavelength different from the first wavelength. For example, referring to FIG. 7, the first light emitting devices 121 and the second light emitting devices 122 may be spaced apart from the light receiver 130 across the light receiver 130 and disposed around the light receiver 130. On the other hand, light receivers may be spaced apart from first light emitting device and second light emitting devices across the first light emitting devices and the second light emitting devices and disposed around the first light emitting devices and the second light emitting devices.

The processor 140 may include various processing circuitry configured for controlling an overall operation of the oxygen saturation measuring apparatus 100.

For example, the processor 140 may filter a frequency component corresponding to motion detected by the sensor 110 from a signal generated by the light receiver 130, detect a pulse frequency from the filtered signal, and determine oxygen saturation of a target object using the filtered signal and the detected pulse frequency.

For example, the processor 140 may determine oxygen saturation based on light corresponding to at least two wavelengths received from the light receiver 130. Hereinafter, for convenience of description, light emitted from a plurality of light emitting devices will be referred to as red light R and infrared ray IR. However, the present disclosure is not limited to the case in which two wavelengths of the red light R and infrared ray IR are used and it may be possible to use three or more wavelengths.

The processor 140 may control the light emitter 120 to emit the red light R and the infrared ray IR to the target object at different time points and separate a signal by the red light R and a signal by the infrared ray IR from a signal generated from the light receiver 130 based on the time points at which the red light R and the infrared ray IR are mitted.

The processor 140 may primarily filter high-frequency and low-frequency signals that are not applied as a bio signal from each of the signal by the red light R and the signal by the infrared ray IR.

In order to eliminate and/or reduce noise by motion from the primarily filtered signal, the processor 140 may filter a frequency component corresponding to motion detected by the sensor 110. For example, the processor 140 may perform second filtering of eliminating and/or reducing a motion artifact due to motion from each of the signal by the red light R and the signal by the infrared ray IR using a motion signal as a reference.

For example, in order to filter motion artifact due to motion, the processor 140 may use an adaptive filter. The adaptive filter may, for example, use an algorithm of estimating a coefficient of a filter every time unit in which a non-stationary signal, of which statistical characteristics are changed as time elapses, and a sample of the signal are input and research has been conducted into various types of filters. For example, various adaptive filtering algorithms such as, for example, and without limitation, a steepest descent algorithm, a least mean square (LMS) algorithm, and a recursive least square (RLS) algorithm may be used.

In addition, the processor 140 may separate an alternating current (AC) component as a pulsation component indicated by heartbeat in a signal from which motion artifact is removed, that is, a secondarily filtered signal and a direct current (DC) component indicated by panniculus including venous blood, blood of capillary, and non-pulsation arterial blood.

For example, a DC component extracted through a low pass filter with a predetermined cutoff frequency may be separated. In addition, a weak AC component may be amplified to a predetermined size through an amplifier.

The processor 140 may detect a pulse frequency of a target subject from the signal from which motion artifact is removed and/or reduced, for example, the secondarily filtered signal. The pulse frequency may be referred to as a heart rate. The pulse frequency may be detected from the secondarily filtered signal via various frequency tracking algorithms. For example, various frequency tracking algorithms such as, for example, and without limitation, an adaptive infinite impulse response bandpass filter (IIR-BPF), a direct frequency estimation algorithm, and an adaptive pisarenko algorithm may be used.

In this example, the processor 140 may detect the pulse frequency from each of the secondarily filtered signal by the red light R and the secondarily filtered signal by the infrared ray IR. The pulse frequency detected from each signal may be used to reinforce only a pulsation component from the secondarily filtered signal.

The processor 140 may also use a pulse frequency detected from only any one of the secondarily filtered signal by the red light R and the secondarily filtered signal by the infrared ray IR instead of detecting a pulse frequency from each of the two signals.

Although a waveform of the signal of the red light R and a waveform of the signal of the infrared ray IR have a difference in terms of a pulse frequency due to a difference in skin transmittance based on a wavelength, both signals originate from the same environment with respect to the same target subject and, thus, the difference between both signals is slight. Accordingly, the pulse frequency detected from any one of the signals may be used to reinforce a pulsation component in another signal.

The processor 140 may separate a signal component corresponding to the detected pulse frequency from the signal from which motion artifact is removed, for example, the secondarily filtered signal by the red light R using the pulse frequency. For example, the used pulse frequency may be detected from the secondarily filtered signal by the red light R or the secondarily filtered signal by the infrared ray IR.

Similarly, the processor 140 may separate a signal component corresponding to the detected pulse frequency from the signal from which motion artifact is removed, For example, the secondarily filtered signal by the infrared ray IR using the pulse frequency. In this example, the pulse frequency may be detected from the secondarily filtered signal by the red light R or the secondarily filtered signal by the infrared ray IR.

For example, the signal component corresponding to the pulse frequency may be separated through a comb filter corresponding to the detected pulse frequency. For example, a signal component corresponding to a heart rate may be reinforced. The processor 140 may square the separated signal component to calculate power (hereinafter, referred to as AC power). Accordingly, the calculated AC power may represent absorption of a pulsation component caused by arterial blood that is affected by contraction and release of heart.

As described above, when a comb filter is used, only a signal component corresponding to the pulse frequency may be separated and reinforced even under noise by an external light source or motion and AC power of the calculated separated signal may be calculated and, thus, oxygen saturation may be advantageously acquired without detection of a peak and a valley unlike in the conventional case.

The processor 140 may determine oxygen saturation based on (AC power)$_R$ corresponding to the red light R and (AC power)$_{IR}$ corresponding to the infrared ray IR. For example, an absorption ratio according to two different wavelengths may be measured to measure oxygen saturation. Two different wavelengths may have different absorptions with respect to hemoglobin with oxygen and hemoglobin without oxygen and, thus, oxygen saturation may be determined through the ratio. The oxygen saturation may be determined according to Equations (1) and (2) below acquired according to the Beer-Lambert rule.

Equation (1) below may be acquired through a correlation graph based on a value of a ratio of normalized pulsation components of two light beams with different wavelengths and a periodically obtained oxygen saturation value in blood.

$$\text{oxygen saturation (SpO}_2\text{)}=X+Y\Phi \quad (1)$$

(X, Y: optical characteristic constant)

$$\Phi=A_R/A_{IR} \quad (2)$$

($A_R$ is absorption of red light and $A_{IR}$ is absorption of infrared light)

Here, $A_R$ may be obtained via normalization of the aforementioned calculated (AC power)$_R$ with power of a DC component separated from a signal of the previously secondary filtered red light and $A_{IR}$ may be obtained via normalization of the aforementioned calculated (AC power)$_{IR}$ with power of a DC component separated from a signal of the previously secondary filtered infrared light.

The oxygen saturation measuring apparatus 100 may further include a display (not shown) and the processor 140 may control the display to display the aforementioned determined oxygen saturation.

The display may be embodied as, for example, a liquid crystal display (LCD) and, as necessary, the display may be embodied as a cathode-ray tube (CRT), a plasma display panel (PDP), organic light emitting diodes (OLEDs), a transparent OLED (TOLED), or the like, but is not limited thereto. In addition, the display may be embodied in the form of a touchscreen for detecting touch manipulation of a user.

The processor 140 may control the display to display a signal from which a pulsation component is removed and provide heart rate information according to the pulse frequency to a user through the display.

The oxygen saturation measuring apparatus 100 may include a communicator (not shown) including communication circuitry for transmitting the determined oxygen saturation, the filtered signal, or heart rate information to another electronic device so as to provide the information to another electronic device.

The communicator may include various communication circuitry in, for example, the form of chips for supporting wired and wireless communication. For example, the communicator may include various communication circuitry, such as, for example, and without limitation, one or more of a WiFi chip, a Bluetooth chip, and a wireless communication chip. The WiFi chip and the Bluetooth chip may perform communication using a WiFi method and a Bluetooth method, respectively. The wireless communication chip may refer to a chip that performs communication according to various communication standards such as IEEE, Zigbee, $3^{rd}$ generation (3G), $3^{rd}$ generation partnership project (3GPP), and long term evolution (LTE). In addition, the communication may further include a near field communication (NFC) chip that is operated using an NFC method.

Figure 8:
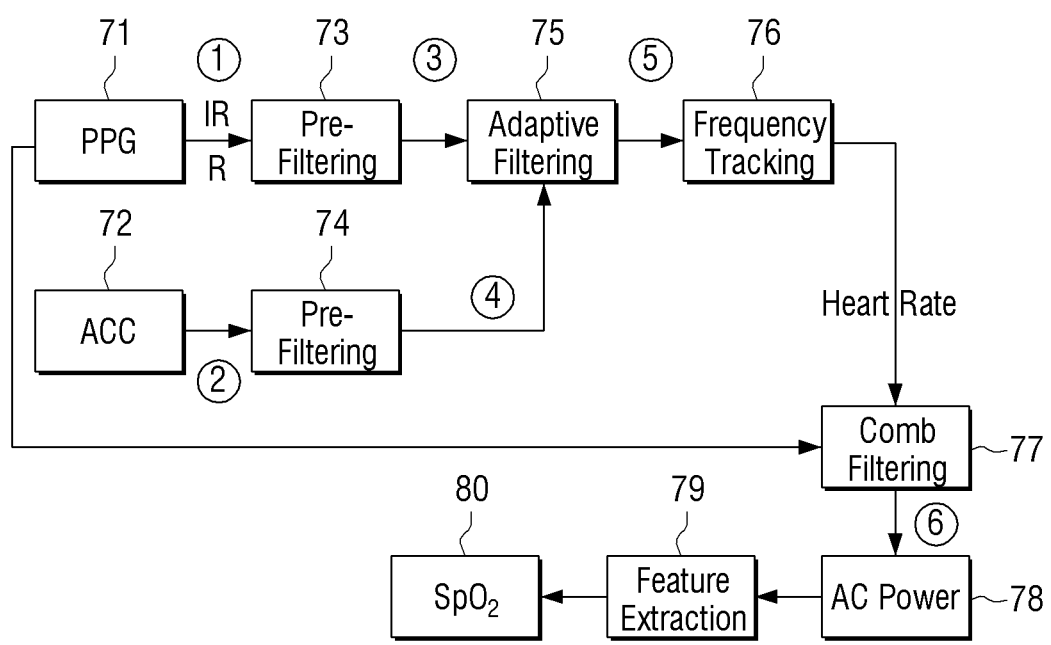
FIG. 8 is a diagram illustrating an example signal processing method of an oxygen saturation measuring apparatus according to an example embodiment of the present disclosure.

FIG. 8 is a diagram illustrating an example signal processing method of the oxygen saturation measuring apparatus 100 according to an example embodiment of the present disclosure and FIGS. 9A, 9B, 9C, 9D, 9E and 9F are diagrams illustrating signals processed in respective operations of FIG. 8.

Figure 9A:
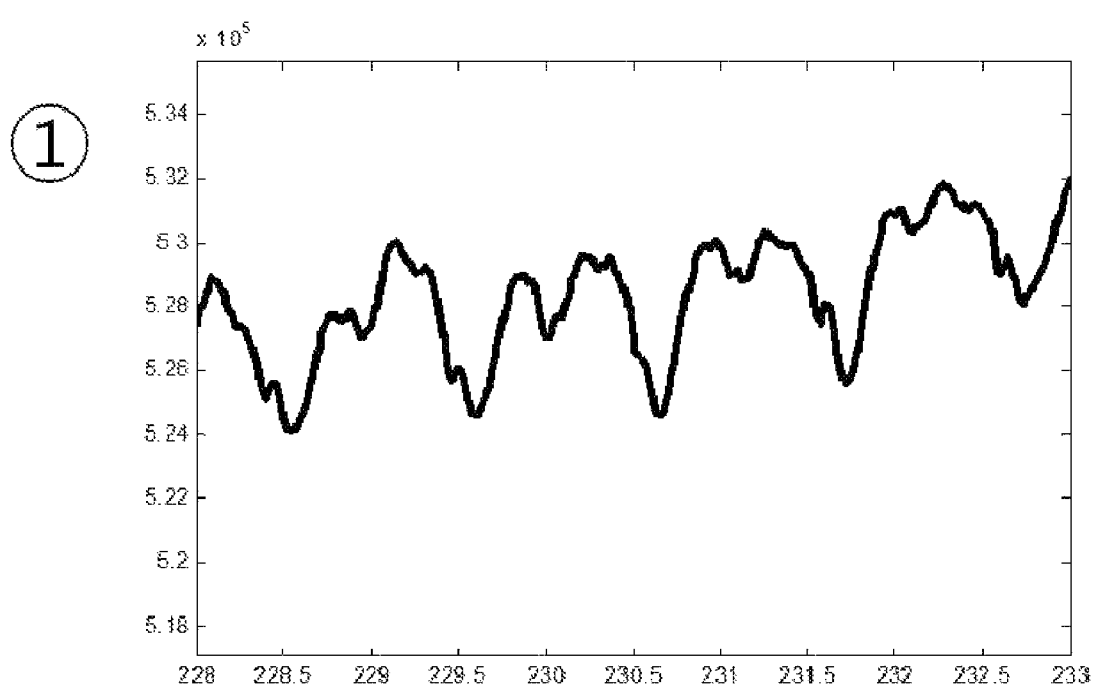
FIGS. 9A, 9B, 9C, 9D, 9E and 9F are diagrams illustrating signals processed in respective operations of FIG. 8.

Referring to FIG. 8, in an operation of block 71, the oxygen saturation measuring apparatus 100 may receive a photoplethysmographic (PPG) signal through the light receiver 130. The PPG signal may include a signal by the red light R and a signal by the infrared ray IR. In addition, the processor 140 may separate the red light R and the infrared ray IR from the PPG signal based on time information at which the red light R and the infrared ray IR are emitted. FIG. 9A illustrates a PPG signal and, for convenience, illustrates only a signal by any one of the red light R and the infrared ray IR.

Figure 9B:
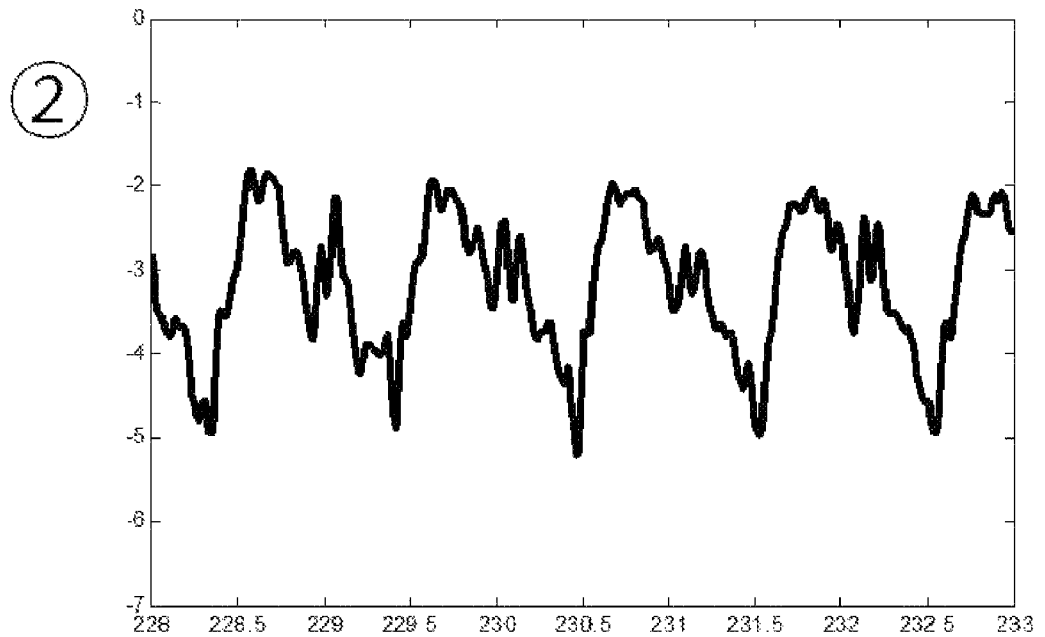

In an operation of block 72, the oxygen saturation measuring apparatus 100 may receive a signal corresponding to motion detected by the sensor 110. FIG. 9B illustrates a signal corresponding to the detected motion. Comparing FIGS. 9A and 9B, it may be seen that a PPG signal has a similar form to motion. For example, the PPG signal includes motion artifact due to motion.

Figure 9C:
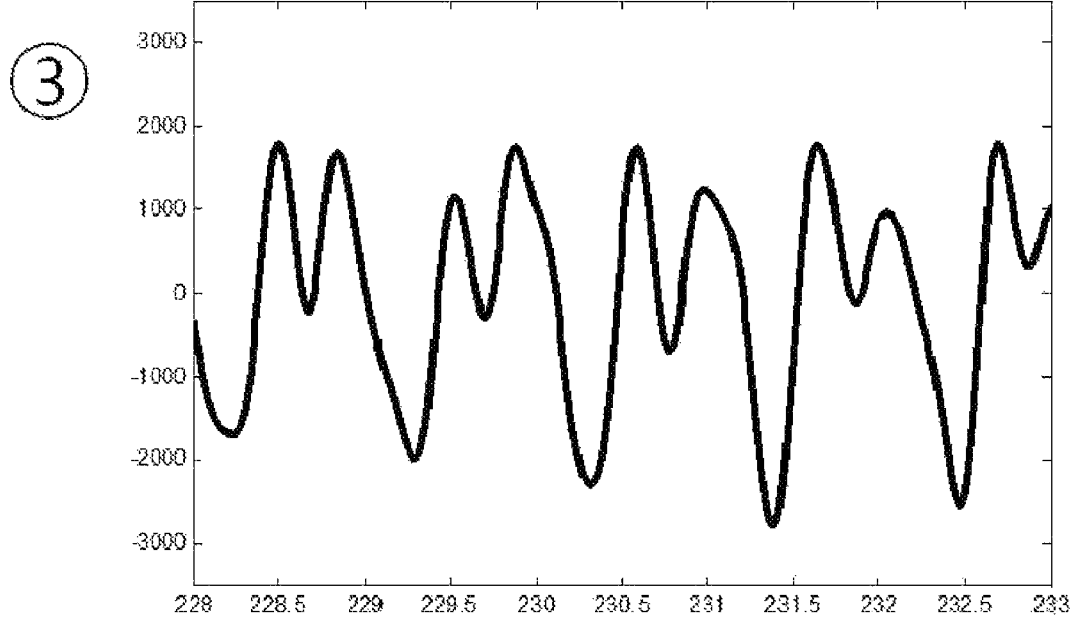

In an operation of block 73, the oxygen saturation measuring apparatus 100 may perform pre-filtering on the PPG signal. For example, filtering may be performed on high frequency and low frequency signals which are not capable of being applied as a bio signal. FIG. 9C illustrates a pre-filtered PPG signal.

Figure 9D:
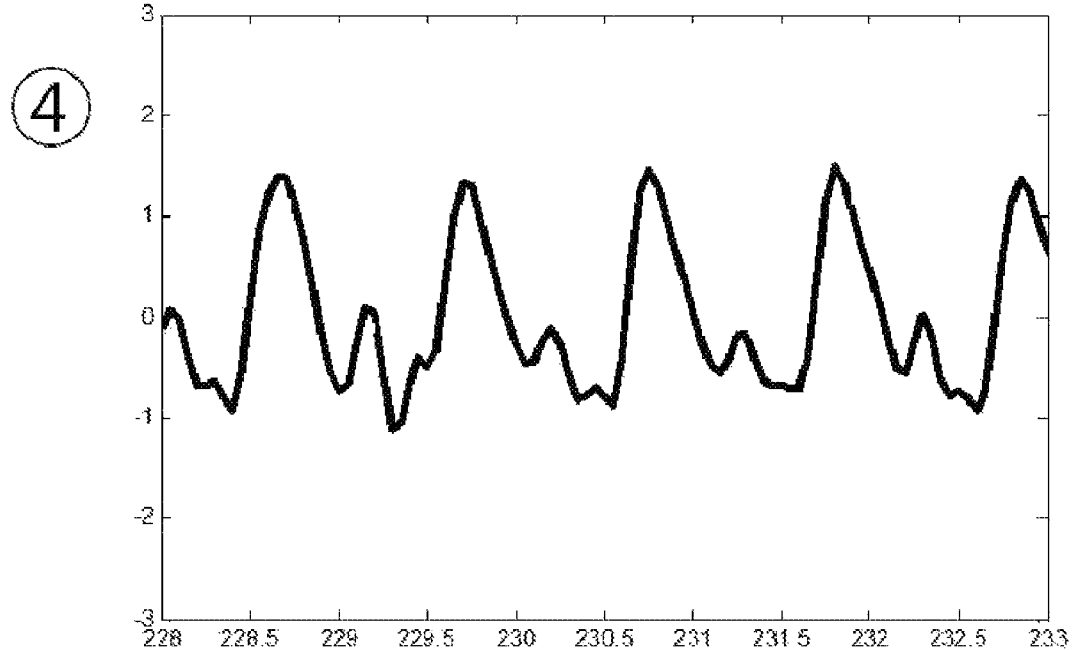

In an operation of block 74, the oxygen saturation measuring apparatus 100 may perform pre-filtering on a signal corresponding to motion. FIG. 9D illustrates a signal obtained by pre-filtering a signal corresponding to motion.

Comparing FIGS. 9C and 9D, it may be seen that a PPG signal has a similar form to motion. Accordingly, it may be necessary to filter motion artifact due to motion from the PPG signal.

In an operation of block 75, the oxygen saturation measuring apparatus 100 may perform adaptive filtering in order to remove and/or reduce a motion artifact due to motion from pulse wave signals of the red light R and the infrared ray IR with reference to a motion signal. The adaptive filter may, for example, use an algorithm of estimating a coefficient of a filter every time unit in which a non-stationary signal, of which statistical characteristics are changed as time elapses, and a sample of the signal are input and research has been conducted into various types of filters. In an operation of block 75, various adaptive filtering algorithms such as, for example, and without limitation, a steepest descent algorithm, a least mean square (LMS) algorithm, and a recursive least square (RLS) algorithm may be used.

Figure 9E:
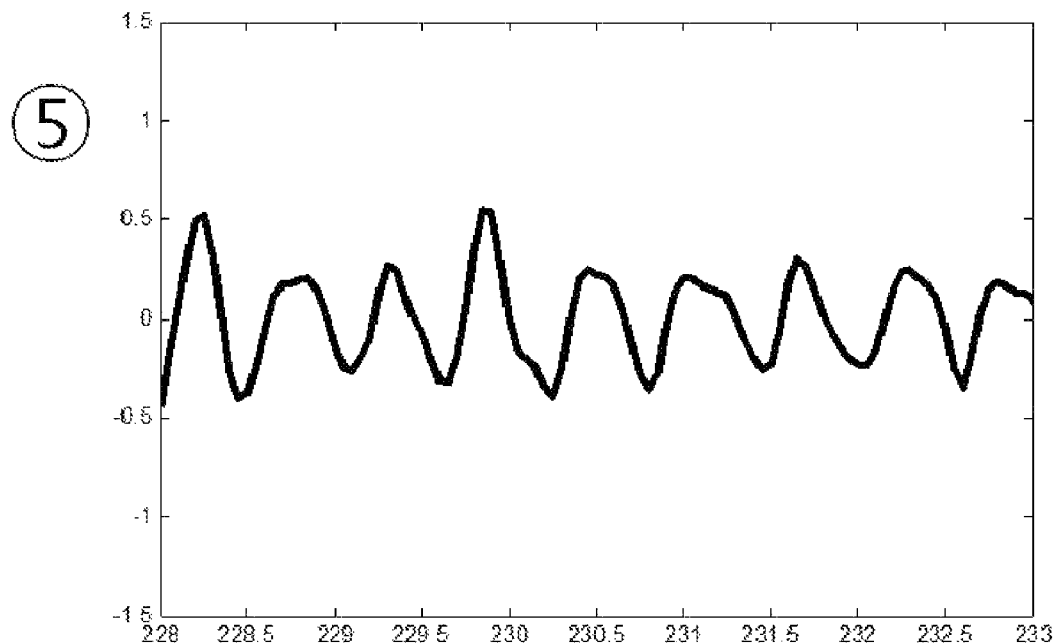

FIG. 9E illustrates an adaptively filtered signal, for example, a signal from which noise due to motion is removed. Referring to FIG. 9E, the signal from which noise due to motion is removed may have a similar frequency to an actual heart beat.

In an operation of block 76, the oxygen saturation measuring apparatus 100 may track a pulse frequency via frequency tracking from a signal from which noise due to motion is removed so as to detect a pulse frequency. In an operation of block 76, various frequency tracking algorithms such as, for example, and without limitation, an adaptive infinite impulse response bandpass filter (IIR-BPF), a direct frequency estimation algorithm, and an adaptive pisarenko algorithm may be used. The pulse frequency may be represented using a heart rate. The oxygen saturation measuring apparatus 100 may detect a pulse frequency from both signals corresponding to the red light R and the infrared ray IR or detect a pulse frequency from a signal corresponding to any one of the red light R and the infrared ray IR.

Figure 9F:
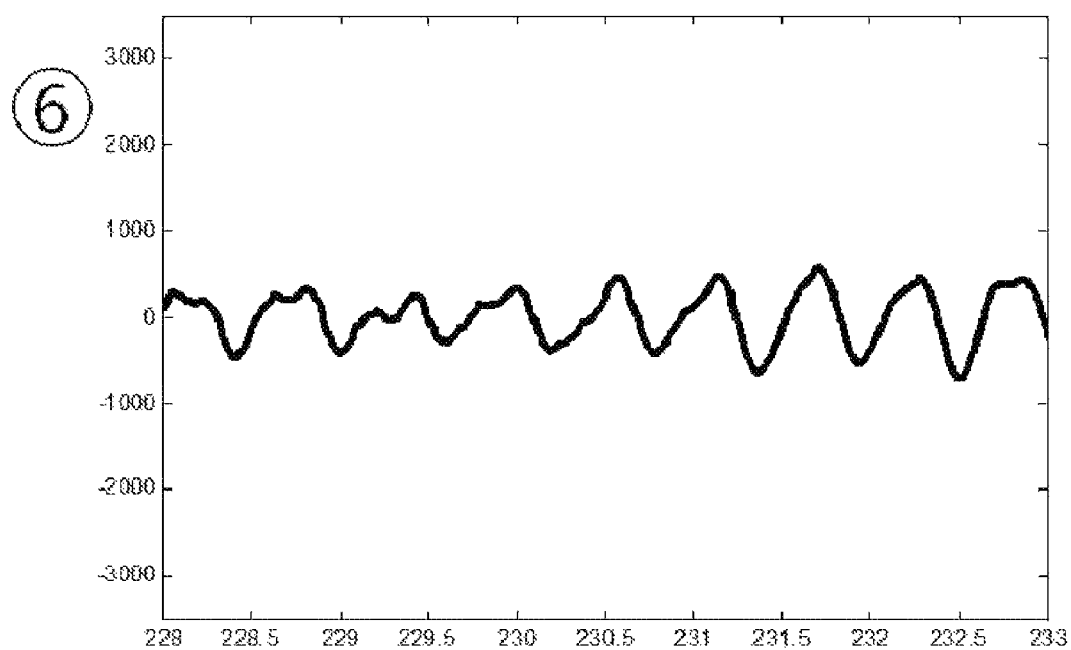

In an operation of block 77, the oxygen saturation measuring apparatus 100 may remove and/or reduce the remaining artifacts via comb filtering from the signal from which noise due to motion is removed in block 75 and reinforce only a pulsation component using the detected pulse frequency. For example, a comb filter may be used to in order to reinforce a signal corresponding to harmonic components of the detected pulse frequency and to reduce the remaining components to noise. FIG. 9F illustrates a PPG signal transmitted through a comb filter.

In an operation of block 78, the oxygen saturation measuring apparatus 100 may acquire AC power of a pulsation component that is reinforced through a comb filter. For example, power $(AC\ Power)_R$ of a pulsation component corresponding to the red light R may be acquired and power $(AC\ Power)_{IR}$ of a pulsation component corresponding to the infrared ray IR may be acquired.

In an operation of block 79, the oxygen saturation measuring apparatus 100 may calculate a ratio of $(AC\ Power)_R$ and $(AC\ Power)_{IR}$. In detail, $(AC\ Power)_R$ may be normalized with power of a DC component at a signal corresponding to the red light R, $(AC\ Power)_{IR}$ may be normalized with power of a DC component at a signal corresponding to the infrared ray IR and, then, feature extraction for calculating a ratio $\Phi$ of the normalized values may be performed.

In an operation of block 80, the oxygen saturation measuring apparatus 100 may insert the aforementioned acquired ratio value to a predetermined equation ($SpO_2$=X+ Y$\Phi$) to determine oxygen saturation.

The determined oxygen saturation may be displayed in a display of the oxygen saturation measuring apparatus 100 or output as voice through a speaker so as to provide information on oxygen saturation to a user.

According to the above oxygen saturation measurement, when it is not possible to detect a peak and a valley in a pulse wave signal due to influence of noise, absorption may be advantageously acquired without detection of a peak and a valley and, motion artifact due to motion of the oxygen saturation measuring apparatus 100 may be removed and, thus, oxygen saturation may be advantageously measured more accurately.

FIG. 10 is a flowchart illustrating an example method of measuring oxygen saturation of the oxygen saturation measuring apparatus 100 according to an example embodiment of the present disclosure.

Referring to FIG. 10, the oxygen saturation measuring apparatus 100 may detect motion (S1010). The oxygen saturation measuring apparatus 100 may detect motion via, for example, an acceleration sensor, a geomagnetic sensor, a gyro sensor, or the like, which are installed in the oxygen saturation measuring apparatus 100.

The oxygen saturation measuring apparatus 100 may emit light to a target subject (S1020). The oxygen saturation measuring apparatus 100 may use two or more light sources with different wavelengths as a light source and, in detail, may select a light source with a wavelength of a range of a large absorption difference between hemoglobin combined with oxygen and hemoglobin that is not combined with oxygen. For example, a red light LED of 660 nm and an infrared LED of 940 nm.

In this example, the oxygen saturation measuring apparatus 100 may gradually blink each LED. A blinking period, a blinking duration, and a blinking order may be set.

The oxygen saturation measuring apparatus 100 may receive light that is reflected by a target subject or transmitted through the target subject and generate a signal (S1030). For example, a light receiver of the oxygen saturation measuring apparatus 100 may receive light, generate a current signal, and re-convert the current signal into a voltage waveform.

The oxygen saturation measuring apparatus 100 may filter a frequency component corresponding to motion detected by the aforementioned acceleration sensor and so on from the signal generated by the light receiver (S1040).

When the oxygen saturation measuring apparatus 100 includes a first light emitting device for emitting light of a first wavelength and a second light emitting device for emitting light of a second wavelength, the oxygen saturation measuring apparatus 100 may filter a frequency component corresponding to the motion detected from the first signal corresponding to light of the first wavelength and filter a frequency component corresponding to the motion detected from the second signal corresponding to light of the second wavelength different form the first wavelength.

The oxygen saturation measuring apparatus 100 may detect a pulse frequency from the filtered signal and determine oxygen saturation of a target subject using the filtered signal and the detected pulse frequency (S1050).

For example, the filtered signal may include a DC component relate to vein, tissue, or the like, and an AC component by a pulsation component of arterial blood. In this case, the oxygen saturation measuring apparatus 100 may determine an average of pulsation components using the DC component.

The oxygen saturation measuring apparatus 100 may detect a first pulse frequency from the aforementioned filtered first signal and detect a second pulse frequency from the aforementioned filtered second signal. The pulse frequency may be detected with respect to only one of the first signal and the second signal.

The oxygen saturation measuring apparatus 100 may separate a signal component corresponding to the detected pulse frequency from the filtered signal. For example, the first signal component corresponding to the first pulse frequency or the second pulse frequency may be separated from the aforementioned filtered first signal and the second signal component corresponding to the first pulse frequency or the second pulse frequency may be separated from the aforementioned filtered second signal.

In this example, the signal components may be separated through a comb filter corresponding to the detected pulse frequency.

In addition, the oxygen saturation measuring apparatus 100 may determine oxygen saturation of a target subject based on the separated signal components. For example, the oxygen saturation may be determined based on a ratio between a signal component by a first wavelength and a signal component by a second wavelength, that is, a ratio of a pulsation component by the first wavelength and a pulsation component by the second wavelength.

Conventionally, since a peak and a valley need to be detected in a pulse according to each heartbeat in the time domain, the result is greatly affected by a signal to noise ratio (SNR) of a signal. For example, in environments outside a hospital, since an external light source such as sunlight or lighting is major influence and motion artifact due to motion such as arm motion or walking is a major influence, it is not possible to accurately detect a peak and a valley and, accordingly, there is a problem in that accurately of oxygen saturation is degraded. For example, when a reflection type sensor needs to be used on a body surface like a wrist watch, it is difficult to ensure a robust contact state between a sensor and a skin surface as compared with a transmission type sensor used in the form of a clip at a finger and an SNR of a pulse wave signal measured by applying relatively large motion is remarkably lowered and, thus, there is a problem in that detected peak and valley values are not accurate.

On the other hand, according to the aforementioned example embodiments of the present disclosure, oxygen saturation may be more robustly measured with respect to noise caused by an external light source, a contact state between a finger and a sensor, or motion than a conventional method of measuring oxygen saturation. For example, when a reflection type sensor is used instead of a distal end part such as the finger or earlobe, excellent measurement performance of oxygen saturation may be achieved with respect to a pulse wave signal of a lower SNR than a transmission type sensor and an oxygen saturation measurement function with high accuracy may be achieved via a mobile device and a wearable device. In addition, a pre-processor may provide a more accurate pulse frequency tracking function even in a noise environment such as motion load so as to provide a accurate heart rate during motion.

In addition, conventionally, there is an attempt to overcome influence of noise caused by an external light source and motion artifact through domain conversion of a signal in the time domain into the frequency domain using a scheme such as fast Fourier transform (FFT) and auto regressive model (AR). However, according to example embodiments of the present disclosure, a frequency tracking algorithm and an adaptive filter may be used in the time domain without using of the aforementioned scheme with high computational complexity and, thus, it may advantageously lower algorithm complexity and more easily apply the algorithm to a mobile product.

The aforementioned various example embodiments of the present disclosure may be embodied in a computer or similar-device readable recording medium in a hardware manner, a software manner, or a combination of the hardware manner and the software manner. In a hardware configuration, the aforementioned example embodiment of the present disclosure may be achieved by at least one of a dedicated processor, application specific integrated circuits (ASICs), digital signal processors (DSPs), digital signal processing devices (DSDPs), programmable logic devices (PLDs), field programmable gate arrays (FPGAs), processors, controllers, microcontrollers, microprocessors, an electric unit for other functions. Some example embodiments, the various example embodiments of the present disclosure may be embodied by the processor 140. In a software configuration, the example embodiments of the procedures and functions described in the disclosure may be embodied by separate software modules. Each of the software modules may perform one or more functions and operations described in the disclosure.

The oxygen saturation measuring method of an oxygen saturation apparatus according to the aforementioned various example embodiments of the present disclosure may be stored in a non-transitory readable medium. The non-transitory readable medium may be installed and used in various devices.

The non-transitory readable medium is a medium that semi-permanently stores data and from which data is readable by a device. For example, the aforementioned various applications or programs may be stored in the non-transitory readable medium, for example, a compact disc (CD), a digital versatile disc (DVD), a hard disc, a bluray disc, a universal serial bus (USB), a memory card, a read only memory (ROM), and the like.

For example, a program code for performing detecting motion of an oxygen saturation measuring apparatus, emitting light to a target subject, receiving light reflected from the target subject or transmitted through the target subject to generated, filtering a frequency component corresponding to the detected motion in the signal, detecting a pulse frequency from the filtered signal, and determining oxygen saturation of the target subject using the filtered signal and the detected pulse frequency may be stored in a non-transitory readable medium, and may be provided.

The foregoing example embodiments and advantages are merely examples and are not to be understood as limiting the present disclosure. The present teaching can be readily applied to other types of apparatuses. Also, the description of the example embodiments of the present disclosure is intended to be illustrative, and not to limit the scope of the claims, and many alternatives, modifications, and variations will be apparent to those skilled in the art.

What is claimed is:

1. An oxygen saturation measuring apparatus:
   a sensor configured to detect motion of the oxygen saturation measuring apparatus;
   a plurality of light emitters comprising light emitting circuitry configured to emit light to a target subject;
   a single light receiver comprising light receiving circuitry configured to receive one or more of light reflected by the target subject or light transmitted through the target subject to generate a signal, wherein the plurality of light emitters are disposed around the single light receiver; and
   a processor configured to pre-filter each of a motion signal from the sensor and a PPG signal from the light receiver to form respective pre-filtered signals, perform adaptive filtering to filter a frequency component corresponding to the detected motion in the signal to form a motion filtered signal from the pre-filtered signals, to perform frequency tracking to detect a pulse frequency from the motion filtered signal, and to determine oxygen saturation of the target subject using the motion filtered signal and the detected pulse frequency.

2. The oxygen saturation measuring apparatus as claimed in claim 1, wherein the processor is configured to separate a signal component corresponding to the detected pulse frequency from the motion filtered signal and to determine oxygen saturation of the target subject based on the separated signal component.

3. The oxygen saturation measuring apparatus as claimed in claim 2, wherein the processor is configured to separate the signal component from the motion filtered signal through a comb filter corresponding to the detected pulse frequency.

4. The oxygen saturation measuring apparatus as claimed in claim 1, wherein the light emitting circuitry comprises a first light emitting device for emitting light of a first wavelength and a second light emitting device for emitting light of a second wavelength different from the first wavelength.

5. The oxygen saturation measuring apparatus as claimed in claim 4, wherein the processor, in forming the motion filtered signal, is configured to filter a frequency component corresponding to the detected motion in a signal corresponding to light of the first wavelength to form a filtered first signal, to filter a frequency component corresponding to the detected motion in a second signal corresponding to light of the second wavelength to form a filtered second signal, to detect a first pulse frequency from the filtered first signal, to separate a first signal component corresponding to the first pulse frequency from the filtered first signal, to separate a second signal component corresponding to first pulse frequency from the filtered second signal, and to determine oxygen saturation of the target subject based on the first signal component and the second signal component.

6. The oxygen saturation measuring apparatus as claimed in claim 4, wherein the processor, in forming the motion filtered signal, is configured to filter a frequency component corresponding to the detected motion in a first signal corresponding to light of the first wavelength to form a filtered first signal, to filter a frequency component corresponding to the detected motion in a second signal corresponding to light of the second wavelength to form a filtered second signal, to detect a first pulse frequency from the filtered first signal, to detect a second pulse frequency from the filtered second signal, to separate a first signal component corresponding to the first pulse frequency from the filtered first signal, to separate a second signal component corresponding to the second pulse frequency from the filtered second signal, and to determine oxygen saturation of the target subject based on the first signal component and the second signal component.

7. The oxygen saturation measuring apparatus as claimed in claim 1, wherein the sensor comprises at least one of: an acceleration sensor, a gyro sensor, and a geomagnetic sensor.

8. The oxygen saturation measuring apparatus as claimed in claim 1, further comprising a display configured to display the determined oxygen saturation.

9. The oxygen saturation measuring apparatus as claimed in claim 8, wherein the processor is configured to control the display to display the filtered signal.

10. The oxygen saturation measuring apparatus as claimed in claim 8, wherein the processor is configured to control the display to display information on the detected pulse frequency.

11. The oxygen saturation measuring apparatus as claimed in claim 1, wherein the oxygen saturation measuring apparatus comprises a smartphone or a wearable device.

12. A method of measuring oxygen saturation by an oxygen saturation measuring apparatus, the method comprising:
    detecting motion of the oxygen saturation measuring apparatus;
    emitting light to a target subject from a plurality of light emitters;
    a single light receiver receiving one or more of light reflected by the target subject or light transmitted through the target subject to generate a signal, wherein the plurality of light emitters are disposed around the single light receiver;
    pre-filtering each of a motion signal from a sensor and a PPG signal from said receiving to form respective pre-filtered signals;
    performing adaptive filtering to filter a frequency component corresponding to the detected motion in the signal to form a motion filtered signal from the pre-filtered signals; and
    performing frequency tracking to detect a pulse frequency from the motion filtered signal and determining oxygen saturation of the target subject using the motion filtered signal and the detected pulse frequency.

13. The method according to claim 12, wherein the determining of the oxygen saturation comprises separating a signal component corresponding to the detected pulse frequency from the filtered signal and determining oxygen saturation of the target subject based on the separated signal component.

14. The method according to claim 13, wherein the determining of the oxygen saturation comprises separating the signal component from the filtered signal through a comb filter corresponding to the detected pulse frequency.

15. The method according to claim 12, wherein the emitting light to a target subject comprises emitting light of a first wavelength and light of a second wavelength different from the first wavelength to the target subject.

16. The method according to claim 15, wherein:
the filtering comprises filtering a frequency component corresponding to the detected motion in a first signal corresponding to light of the first wavelength to form a filtered first signal, and filtering a frequency component corresponding to the detected motion in a second signal corresponding to the light of second wavelength to form a filtered second signal; and
the determining of the oxygen saturation comprises detecting a first pulse frequency from the filtered first signal, separating a first signal component corresponding to the first pulse frequency from the filtered first signal, separating a second signal component corresponding to the first pulse frequency from the filtered second signal, and determining oxygen saturation of the target subject based on the first signal component and the second signal component.

17. The method according to claim 15, wherein:
the filtering comprises filtering a frequency component corresponding to the detected motion in a first signal corresponding to light of the first wavelength to form a filtered first signal, and filtering frequency component corresponding to the detected motion in a second signal corresponding to light of the second wavelength to form a filtered second signal;
the determining of the oxygen saturation comprises detecting a first pulse frequency from the filtered first signal, detecting a second pulse frequency from the filtered second signal, separating a first signal component corresponding to the first pulse frequency from the filtered first signal, separating a second signal component corresponding to the second pulse frequency from the filtered second signal, and determining oxygen saturation of the target subject based on the first signal component and the second signal component.

18. The method according to claim 12, further comprising displaying the determined oxygen saturation.

19. The method according to claim 12, further comprising displaying the filtered signal.

20. A non-transitory computer readable recording medium having recorded thereon a program which, when executed by one or more processors, causes the one or more processors to perform operations comprising:
detecting motion of an oxygen saturation measuring apparatus;
emitting light to a target subject from a plurality of light emitters;
a single light receiver receiving one or more of light reflected by the target subject or light transmitted through the target subject to generate a signal, wherein the plurality of light emitters are disposed around the single light receiver;
pre-filtering each of a motion signal from a sensor and a PPG signal from said receiving to form respective pre-filtered signals;
performing adaptive filtering to filter a frequency component corresponding to the detected motion in the signal to form a motion filtered signal from the pre-filtered signals; and
performing frequency tracking to detect a pulse frequency from the motion filtered signal and determining oxygen saturation of the target subject using the motion filtered signal and the detected pulse frequency.

* * * * *